(12) United States Patent
Ichinohe et al.

(10) Patent No.: US 8,574,239 B2
(45) Date of Patent: Nov. 5, 2013

(54) INTRAOCULAR LENS INSERTION DEVICE

(75) Inventors: Takashi Ichinohe, Tokyo (JP); Kazunori Kudoh, Tokyo (JP)

(73) Assignee: Hoya Corporation, Tokyo (JP)

( * ) Notice: Subject to any disclaimer, the term of this patent is extended or adjusted under 35 U.S.C. 154(b) by 641 days.

(21) Appl. No.: 12/088,328

(22) PCT Filed: Sep. 26, 2006

(86) PCT No.: PCT/JP2006/319046
§ 371 (c)(1),
(2), (4) Date: Mar. 27, 2008

(87) PCT Pub. No.: WO2007/037223
PCT Pub. Date: Apr. 5, 2007

(65) Prior Publication Data
US 2009/0036898 A1      Feb. 5, 2009

(30) Foreign Application Priority Data

Sep. 28, 2005   (JP) .................................. 2005-282311

(51) Int. Cl.
*A61F 9/00*      (2006.01)
*A61F 2/16*      (2006.01)

(52) U.S. Cl.
USPC ........................................ 606/107; 623/6.12

(58) Field of Classification Search
USPC ................ 606/107, 166, 108; 623/6.12, 6.11; 206/5.1
See application file for complete search history.

(56) References Cited

U.S. PATENT DOCUMENTS

| | | |
|---|---|---|
| 2,761,446 A | 9/1956 | Reed |
| 4,205,747 A | 6/1980 | Gilliam et al. |
| 4,269,307 A | 5/1981 | LaHaye |
| 4,423,809 A | 1/1984 | Mazzocco |
| 4,573,998 A | 3/1986 | Mazzocco |
| 4,608,049 A | 8/1986 | Kelman |
| 4,634,423 A | 1/1987 | Bailey |
| 4,681,102 A | 7/1987 | Bartell |
| 4,697,697 A | 10/1987 | Graham et al. |
| 4,699,140 A | 10/1987 | Holmes |
| 4,702,244 A | 10/1987 | Mazzocco |
| 4,715,373 A | 12/1987 | Mazzocco et al. |

(Continued)

FOREIGN PATENT DOCUMENTS

| | | |
|---|---|---|
| DE | 3610925 | 10/1987 |
| DE | 4110278 | 10/1992 |

(Continued)

*Primary Examiner* — Thomas McEvoy
*Assistant Examiner* — Jocelin Tanner
(74) *Attorney, Agent, or Firm* — Henricks, Slavin & Holmes LLP

(57) ABSTRACT

An intraocular lens insertion device for inserting an intraocular lens capable of securely and safely pushing out the lens by a simple structure. An intraocular lens insertion device (1) comprises: a main body (3) having a lens placement portion (8) on which the lens (2) with a pair of loop parts (2b) at its optic part (2a) is placed, a transition portion (12) deforming the lens (2), and a nozzle portion (11) discharging the lens (2); and a lens push-out mechanism (4) pushing out the lens (2) placed on the lens placement portion (8). The lens push-out mechanism (4) comprises a plunger (16) pushing out the lens (2) and a slider (15) having a lens contact part (20) larger than the plunger (16). The slider (15) comprises an operating part (23) projected to the outside of the body (3).

14 Claims, 10 Drawing Sheets

(56) References Cited

U.S. PATENT DOCUMENTS

| | | | |
|---|---|---|---|
| 4,747,404 | A | 5/1988 | Jampel et al. |
| 4,750,498 | A | 6/1988 | Graham |
| 4,759,359 | A | 7/1988 | Willis et al. |
| 4,763,650 | A | 8/1988 | Hauser |
| 4,765,329 | A | 8/1988 | Cumming et al. |
| 4,769,034 | A | 9/1988 | Poley |
| 4,781,719 | A | 11/1988 | Kelman |
| 4,787,904 | A | 11/1988 | Severin |
| 4,819,631 | A | 4/1989 | Poley |
| 4,834,094 | A | 5/1989 | Patton et al. |
| 4,836,201 | A * | 6/1989 | Patton et al. ............ 606/107 |
| 4,862,885 | A | 9/1989 | Cumming |
| 4,880,000 | A | 11/1989 | Holmes et al. |
| 4,919,130 | A | 4/1990 | Stoy et al. |
| 4,934,363 | A | 6/1990 | Smith et al. |
| 4,955,889 | A | 9/1990 | Van Gent |
| 4,976,716 | A | 12/1990 | Cumming |
| 4,988,352 | A | 1/1991 | Poley |
| 4,994,028 | A | 2/1991 | Leonard et al. |
| 5,066,297 | A | 11/1991 | Cumming |
| 5,098,439 | A | 3/1992 | Hill et al. |
| 5,123,905 | A | 6/1992 | Kelman |
| 5,139,501 | A | 8/1992 | Klaas |
| 5,171,241 | A | 12/1992 | Buboltz et al. |
| 5,176,686 | A | 1/1993 | Poley |
| 5,190,552 | A | 3/1993 | Kelman |
| 5,190,553 | A | 3/1993 | Kanert et al. |
| 5,222,972 | A | 6/1993 | Hill et al. |
| 5,242,450 | A | 9/1993 | McDonald |
| 5,259,395 | A | 11/1993 | Li |
| 5,275,604 | A | 1/1994 | Rheinish et al. |
| 5,281,227 | A | 1/1994 | Sussman |
| 5,304,182 | A | 4/1994 | Rheinish et al. |
| 5,354,333 | A | 10/1994 | Kammann et al. |
| 5,395,378 | A | 3/1995 | McDonald |
| 5,425,734 | A | 6/1995 | Blake |
| 5,454,818 | A | 10/1995 | Hambleton et al. |
| 5,468,246 | A | 11/1995 | Blake |
| 5,474,562 | A | 12/1995 | Orchowski et al. |
| 5,494,484 | A | 2/1996 | Feingold |
| 5,496,328 | A | 3/1996 | Nakajima et al. |
| 5,499,987 | A | 3/1996 | Feingold |
| 5,562,676 | A | 10/1996 | Brady et al. |
| 5,571,113 | A | 11/1996 | McDonald |
| 5,578,042 | A | 11/1996 | Cumming |
| 5,582,613 | A | 12/1996 | Brady |
| 5,582,614 | A | 12/1996 | Feingold |
| 5,584,304 | A | 12/1996 | Brady |
| 5,616,148 | A | 4/1997 | Eagles et al. |
| 5,620,450 | A | 4/1997 | Eagles et al. |
| 5,643,275 | A | 7/1997 | Blake |
| 5,643,276 | A | 7/1997 | Zaleski |
| 5,645,534 | A | 7/1997 | Chanoch |
| 5,653,715 | A | 8/1997 | Reich et al. |
| 5,653,753 | A | 8/1997 | Brady et al. |
| 5,702,402 | A | 12/1997 | Brady |
| 5,702,441 | A | 12/1997 | Zhou |
| 5,716,364 | A | 2/1998 | Makker et al. |
| 5,728,075 | A | 3/1998 | Levander |
| 5,728,102 | A | 3/1998 | Feingold et al. |
| 5,735,858 | A | 4/1998 | Makker et al. |
| 5,766,181 | A | 6/1998 | Chambers et al. |
| 5,772,666 | A | 6/1998 | Feingold et al. |
| 5,772,667 | A | 6/1998 | Blake |
| 5,776,138 | A | 7/1998 | Vidal et al. |
| 5,800,442 | A | 9/1998 | Wolf et al. |
| 5,803,925 | A | 9/1998 | Yang et al. |
| 5,807,400 | A | 9/1998 | Chambers et al. |
| 5,810,833 | A | 9/1998 | Brady et al. |
| 5,810,834 | A | 9/1998 | Heyman |
| 5,860,984 | A | 1/1999 | Chambers et al. |
| 5,860,986 | A | 1/1999 | Reich et al. |
| 5,868,751 | A | 2/1999 | Feingold |
| 5,868,752 | A | 2/1999 | Makker et al. |
| 5,873,879 | A | 2/1999 | Figueroa et al. |
| 5,876,406 | A | 3/1999 | Wolf et al. |
| 5,876,407 | A | 3/1999 | Makker et al. |
| 5,876,440 | A | 3/1999 | Feingold |
| 5,891,152 | A | 4/1999 | Feingold |
| 5,902,307 | A | 5/1999 | Feingold et al. |
| 5,919,197 | A | 7/1999 | McDonald |
| 5,921,989 | A | 7/1999 | Deacon et al. |
| 5,928,245 | A | 7/1999 | Wolf et al. |
| 5,941,886 | A | 8/1999 | Feingold |
| 5,942,277 | A | 8/1999 | Makker et al. |
| 5,944,725 | A | 8/1999 | Cicenas |
| 5,947,974 | A | 9/1999 | Brady et al. |
| 5,947,975 | A | 9/1999 | Kikuchi et al. |
| 5,957,748 | A | 9/1999 | Ichiha |
| 6,001,107 | A | 12/1999 | Feingold |
| 6,010,510 | A | 1/2000 | Brown et al. |
| 6,022,358 | A | 2/2000 | Wolf et al. |
| 6,048,348 | A | 4/2000 | Chambers et al. |
| 6,051,000 | A | 4/2000 | Heyman |
| 6,056,757 | A | 5/2000 | Feingold et al. |
| 6,056,758 | A | 5/2000 | Vidal et al. |
| 6,059,791 | A | 5/2000 | Chambers |
| 6,074,397 | A | 6/2000 | Chambers et al. |
| 6,083,230 | A | 7/2000 | Makker et al. |
| 6,093,193 | A | 7/2000 | Makker et al. |
| 6,129,733 | A | 10/2000 | Brady et al. |
| 6,142,999 | A | 11/2000 | Brady et al. |
| 6,143,000 | A | 11/2000 | Feingold |
| 6,162,229 | A | 12/2000 | Feingold et al. |
| 6,174,315 | B1 | 1/2001 | Chambers et al. |
| 6,214,015 | B1 | 4/2001 | Reich et al. |
| 6,241,737 | B1 | 6/2001 | Feingold |
| 6,248,111 | B1 | 6/2001 | Glick et al. |
| 6,251,114 | B1 | 6/2001 | Farmer et al. |
| 6,254,607 | B1 | 7/2001 | Makker et al. |
| 6,267,768 | B1 | 7/2001 | Deacon |
| 6,283,975 | B1 | 9/2001 | Glick et al. |
| 6,283,976 | B1 | 9/2001 | Portney |
| 6,312,433 | B1 | 11/2001 | Butts |
| 6,334,862 | B1 | 1/2002 | Vidal et al. |
| 6,336,932 | B1 | 1/2002 | Figueroa et al. |
| 6,355,046 | B2 | 3/2002 | Kikuchi et al. |
| 6,371,960 | B2 | 4/2002 | Heyman et al. |
| 6,386,357 | B1 | 5/2002 | Egawa |
| 6,387,101 | B1 | 5/2002 | Butts et al. |
| 6,398,788 | B1 | 6/2002 | Makker et al. |
| 6,406,481 | B2 | 6/2002 | Feingold et al. |
| 6,428,545 | B2 | 8/2002 | Portney |
| 6,447,519 | B1 | 9/2002 | Brady et al. |
| 6,447,520 | B1 | 9/2002 | Ott et al. |
| 6,468,282 | B2 | 10/2002 | Kikuchi et al. |
| 6,471,708 | B2 | 10/2002 | Green |
| 6,491,697 | B1 | 12/2002 | Clark et al. |
| 6,497,708 | B1 | 12/2002 | Cumming |
| 6,500,181 | B1 * | 12/2002 | Portney .............. 606/107 |
| 6,506,195 | B2 | 1/2003 | Chambers et al. |
| 6,537,283 | B2 * | 3/2003 | Van Noy ............ 606/107 |
| 6,540,754 | B2 | 4/2003 | Brady |
| 6,554,839 | B2 | 4/2003 | Brady |
| 6,558,395 | B2 | 5/2003 | Hjertman et al. |
| 6,607,537 | B1 | 8/2003 | Binder |
| 6,629,979 | B1 | 10/2003 | Feingold |
| 6,666,871 | B2 | 12/2003 | Kikuchi et al. |
| 6,679,891 | B2 | 1/2004 | Makker et al. |
| 6,685,740 | B2 | 2/2004 | Figueroa et al. |
| 6,712,848 | B1 | 3/2004 | Wolf et al. |
| 6,723,104 | B2 | 4/2004 | Ott |
| 6,733,507 | B2 | 5/2004 | McNicholas et al. |
| 6,793,674 | B2 | 9/2004 | Zapata |
| 6,858,033 | B2 | 2/2005 | Kobayashi |
| 6,921,405 | B2 | 7/2005 | Feingold et al. |
| 6,923,815 | B2 | 8/2005 | Brady et al. |
| 6,976,989 | B1 | 12/2005 | Vincent |
| 7,014,641 | B2 | 3/2006 | Kobayashi et al. |
| 7,025,782 | B2 | 4/2006 | Kobayashi et al. |
| 7,033,366 | B2 | 4/2006 | Brady |
| 7,037,312 | B2 | 5/2006 | Kikuchi et al. |
| 7,074,227 | B2 * | 7/2006 | Portney .............. 606/107 |
| 7,097,649 | B2 | 8/2006 | Meyer |

(56) References Cited

U.S. PATENT DOCUMENTS

| | | |
|---|---|---|
| 7,131,976 B2 | 11/2006 | Kobayashi et al. |
| 7,156,854 B2 | 1/2007 | Brown et al. |
| 7,348,038 B2 | 3/2008 | Makker et al. |
| 7,422,604 B2 | 9/2008 | Vaquero et al. |
| 7,429,263 B2 | 9/2008 | Vaquero et al. |
| 7,458,976 B2 | 12/2008 | Peterson et al. |
| 7,476,230 B2 | 1/2009 | Ohno et al. |
| 7,494,505 B2 | 2/2009 | Kappelhof et al. |
| 7,645,300 B2 * | 1/2010 | Tsai ............................ 623/6.12 |
| 8,273,122 B2 | 9/2012 | Anderson |
| 8,382,769 B2 | 2/2013 | Inoue |
| 8,460,311 B2 | 6/2013 | Ishii |
| 8,470,032 B2 | 6/2013 | Inoue et al. |
| 8,475,528 B2 | 7/2013 | Ichinohe et al. |
| 8,523,877 B2 | 9/2013 | Ichinohe et al. |
| 8,523,941 B2 | 9/2013 | Ichinohe et al. |
| 2001/0007942 A1 | 7/2001 | Kikuchi et al. |
| 2002/0103490 A1 | 8/2002 | Brady |
| 2002/0151904 A1 | 10/2002 | Feingold et al. |
| 2002/0165610 A1 | 11/2002 | Wadlaock |
| 2002/0193805 A1 | 12/2002 | Ott et al. |
| 2003/0036765 A1 | 2/2003 | Van Noy |
| 2003/0040755 A1 | 2/2003 | Meyer |
| 2003/0050647 A1 | 3/2003 | Brady |
| 2003/0088253 A1 | 5/2003 | Seil |
| 2003/0139749 A1 | 7/2003 | Kikuchi et al. |
| 2003/0181921 A1 | 9/2003 | Jeannin |
| 2003/0195522 A1 | 10/2003 | McNicholas |
| 2003/0212406 A1 | 11/2003 | Kobayashi et al. |
| 2003/0212407 A1 * | 11/2003 | Kikuchi et al. ............... 606/107 |
| 2003/0212409 A1 | 11/2003 | Kobayashi et al. |
| 2004/0111094 A1 | 6/2004 | Meyer |
| 2004/0117012 A1 | 6/2004 | Vincent |
| 2004/0238392 A1 | 12/2004 | Peterson et al. |
| 2004/0243141 A1 | 12/2004 | Brown et al. |
| 2005/0033308 A1 | 2/2005 | Callahan et al. |
| 2005/0049605 A1 * | 3/2005 | Vaquero et al. ............... 606/107 |
| 2005/0049606 A1 | 3/2005 | Vaquero et al. |
| 2005/0125000 A1 | 6/2005 | Tourrette et al. |
| 2005/0182419 A1 | 8/2005 | Tsai |
| 2005/0222578 A1 | 10/2005 | Vaquero |
| 2005/0261703 A1 | 11/2005 | Feingold et al. |
| 2006/0085013 A1 * | 4/2006 | Dusek et al. .................. 606/107 |
| 2006/0142781 A1 | 6/2006 | Pynson et al. |
| 2006/0167466 A1 | 7/2006 | Dusek |
| 2006/0229633 A1 | 10/2006 | Shepherd |
| 2006/0293694 A1 | 12/2006 | Futamura |
| 2008/0033449 A1 | 2/2008 | Cole et al. |
| 2008/0058830 A1 | 3/2008 | Cole et al. |
| 2008/0086146 A1 | 4/2008 | Ishii et al. |
| 2008/0097459 A1 | 4/2008 | Kammerlander et al. |
| 2008/0221584 A1 | 9/2008 | Downer |
| 2009/0043313 A1 | 2/2009 | Ichinohe |
| 2009/0112223 A1 | 4/2009 | Downer et al. |
| 2009/0125034 A1 | 5/2009 | Pynson |
| 2009/0138022 A1 | 5/2009 | Tu et al. |
| 2009/0204122 A1 | 8/2009 | Ichinohe et al. |
| 2009/0216244 A1 | 8/2009 | Pynson |
| 2009/0248031 A1 | 10/2009 | Ichinohe |
| 2010/0161049 A1 | 6/2010 | Inoue |
| 2010/0185206 A1 | 7/2010 | Ichinohe et al. |
| 2010/0217273 A1 | 8/2010 | Someya et al. |
| 2010/0286704 A1 | 11/2010 | Ichinohe et al. |
| 2011/0082463 A1 | 4/2011 | Inoue |
| 2011/0098717 A1 | 4/2011 | Inoue |
| 2011/0264101 A1 | 10/2011 | Inoue et al. |
| 2011/0270264 A1 | 11/2011 | Shoji et al. |
| 2011/0288557 A1 | 11/2011 | Kudo et al. |
| 2012/0022549 A1 | 1/2012 | Someya et al. |
| 2012/0071887 A1 | 3/2012 | Ichinohe et al. |
| 2013/0006259 A1 | 1/2013 | Sanger |
| 2013/0018460 A1 | 1/2013 | Anderson |

FOREIGN PATENT DOCUMENTS

| | | |
|---|---|---|
| EP | 0363213 | 4/1990 |
| EP | 0727966 | 9/2003 |
| EP | 1832247 A1 | 9/2007 |
| EP | 1338254 | 12/2008 |
| FR | 2749752 A | 12/1997 |
| JP | 63-197453 A | 8/1988 |
| JP | 4-212350 A | 8/1992 |
| JP | 5-103808 | 4/1993 |
| JP | 5-103809 | 4/1993 |
| JP | 8-024282 A | 1/1996 |
| JP | 8-505540 | 6/1996 |
| JP | 9-506285 A | 6/1997 |
| JP | 11-113939 A | 4/1999 |
| JP | 11-506357 A | 6/1999 |
| JP | 2000-516487 A | 12/2000 |
| JP | 2000-516488 A | 12/2000 |
| JP | 2001-502563 | 2/2001 |
| JP | 2001-104347 A | 4/2001 |
| JP | 2002-516709 A | 6/2002 |
| JP | 2002-355268 A | 12/2002 |
| JP | 2002-541912 A | 12/2002 |
| JP | 2003-144480 A | 5/2003 |
| JP | 3412106 B2 | 6/2003 |
| JP | 2003-210498 A | 7/2003 |
| JP | 2003-325569 A | 11/2003 |
| JP | 2003-325570 | 11/2003 |
| JP | 2003-325572 | 11/2003 |
| JP | 2004-024854 | 1/2004 |
| JP | 2004-188194 A | 7/2004 |
| JP | 2004-351196 A | 12/2004 |
| JP | 2006-181269 A | 7/2006 |
| JP | 2006-297146 A | 11/2006 |
| JP | 2006-333924 A | 12/2006 |
| JP | 2006-333981 A | 12/2006 |
| JP | 2007-503872 A | 3/2007 |
| JP | 2007-152010 A | 6/2007 |
| JP | 2007-181604 A | 7/2007 |
| JP | 2007-526091 A | 9/2007 |
| JP | 2008-521535 A | 6/2008 |
| JP | 2008-212689 A | 9/2008 |
| WO | WO9407436 A1 | 4/1994 |
| WO | WO9513022 A1 | 5/1995 |
| WO | WO9628122 A1 | 9/1996 |
| WO | WO9715253 A1 | 5/1997 |
| WO | WO9812969 A1 | 4/1998 |
| WO | WO0045746 A1 | 8/2000 |
| WO | WO0062712 A1 | 10/2000 |
| WO | WO02071982 A1 | 9/2002 |
| WO | WO02096322 A1 | 12/2002 |
| WO | WO2005023154 A1 | 3/2005 |
| WO | WO2005070341 A1 | 8/2005 |
| WO | WO2005084588 A1 | 9/2005 |
| WO | WO2006070628 A1 | 7/2006 |
| WO | WO2006080191 A1 | 8/2006 |
| WO | WO2006090531 A1 | 8/2006 |
| WO | WO2007037223 A1 | 4/2007 |
| WO | WO2007097221 A1 | 4/2007 |
| WO | WO2007080869 A1 | 7/2007 |
| WO | WO2008149794 A1 | 12/2008 |
| WO | WO2008149795 A1 | 12/2008 |
| WO | WO2009058929 A1 | 7/2009 |
| WO | WO2009148091 A1 | 12/2009 |
| WO | WO2011126144 A1 | 10/2011 |
| WO | WO2011155636 A1 | 12/2011 |

* cited by examiner

INTRAOCULAR LENS INSERTION DEVICE

TECHNICAL FIELD

The present invention relates to an intraocular lens insertion device that inserts an intraocular lens into an aphakic eye after a cataract operation, or, to an intraocular lens insertion device that inserts a phakic intraocular lens during a refractive surgery.

BACKGROUND ART

In cataract operations, removing an opacified lens by phacoemulsification (PEA) and implanting an intraocular lens after an opacified lens has been removed are widely performed. The types of intraocular lens include a hard intraocular lens with its optic area made of a hard material, such as PMMA, and a soft intraocular lens made of a soft material such as silicone elastomer or soft acrylic. When using a hard intraocular lens, the intraocular lens must be inserted through an incision in the cornea or sclera that is formed so as to have about the same width as the diameter of the optic area. On the other hand, when using a soft intraocular lens, folding of the optic area allows the intraocular lens to be inserted into the eye through an incision that is smaller than the diameter of the optic area. Inserting a lens from a small incision is desirable to reduce the post-surgery corneal astigmatism and infection, so there has been a trend in recent years to favor the soft intraocular lens. In addition, to insert the lens into the eye, there are cases where a special injector is used, said special injector having a structure provided with a long tube through which the lens passes as it is guided into the eye. Using such a special intraocular lens injector makes it possible to insert the lens through an incision smaller than 3 mm.

In addition, preset injectors having the lens set in the injector in advance to eliminate the risk of contamination by microbes during lens handing and of possible operational mistakes during lens handling have recently come to market. Some preset injectors are provided with a holding mechanism that holds the lens inside in a state that does not stress the optic area and with a lens movement mechanism that moves the lens to a position where it can be pushed out by an discharge device so as to transfer the lens from the lens immovable state during shipment to the lens movable state during use (For example, Patent Documents 1 and 2).

However, in the above patent documents 1 or 2, it is necessary to move the lens from the stationary position to a position where it can be pushed out during its use, and there is a fear of yielding operational mistake accompanying the movement operation. As a solution to such problems, there is disclosed an intraocular lens insertion device characterized in that a push-out shaft and a posture control member for preventing the shaft misalignment between the push-out shaft and a lens are arranged in a manner capable of interlocking with each other, and such mutual interlocking is released at a prescribed position (For example, Patent Document 3). In this patent document 3, it is necessary to provide a special mechanism for releasing at a predetermined position the interlocking between the two members: the push-out shaft and the posture control member that are interlocked with each other within a closed space or an injector. Further, there is disclosed another intraocular lens insertion device characterized in comprising a mechanism for laterally compressing a flexible intraocular lens into a small cross-sectional configuration (For example, Patent Document 4).

Patent Document 1: Japanese Patent Application Laid-Open (JP-A) No. 2003-325570
Patent Document 2: JP-A No. 2003-325572
Patent Document 3: JP-A No. 2004-24854
Patent Document 4: JP-A No. 2001-502563

DISCLOSURE OF INVENTION

Problems to be Solved by the Invention

However, even in the above-mentioned Patent Document 3, there is a possibility that the interlocking is started and released outside the prescribed position, giving users a feeling of anxiety. In the case that the interlocking is released outside the prescribed position, for example short of the prescribed position, the posture control member also comes to stop short of the prescribed position. Thus, the position of the push-out shaft cannot be sufficiently controlled, thus leading to a possibility that a lens is pushed out with the axis of the push-out shaft being misaligned. On the other hand, a transition portion for folding a lens needs to be formed gently so that the lens is not subjected to a local load. If the interlocking is released by the contact of the transition portion with the posture control member, the position where the interlocking is released varies by the fluctuation of a slide friction. Accordingly, to perform the start and release of the interlocking at the prescribed portion, physical properties such as tensile strength of the push-out shaft and of the posture control member are limited, and high accuracy is required for each component, thus leading to concerns about high production costs. Furthermore, if the device is assembled with the interlocking of the push-out shaft and the posture control member having already been released beforehand by mistake in a production process, yet it is difficult to notice the assembly defect once it has been assembled, and thus, there has been a concern that it may be shipped as it is.

Moreover, referring to the above-mentioned Patent Document 4, it is primarily featured by the provision of retainers to maintain the opposing side edges of an intraocular lens in a substantially planar orientation so as not to damage the inside of the eye when releasing the intraocular lens in the eye from a compressed state. With such configuration employed, however, there has been a problem that too heavy load may be applied to the lens, which could damage the lens when the intraocular lens is pressed against the fine areas of a lens placing section and a tubular member.

Therefore, in view of the above mentioned problems, an object of the present invention is to provide an intraocular lens insertion device capable of securely and safely pushing out the lens by a simple structure.

Means for Solving the Problems

To achieve the above object, the invention according to a first aspect of the invention is an intraocular lens insertion device characterized in comprising:

a main body comprising a lens placement portion to place an intraocular lens thereon, a transition portion to deform said intraocular lens and a nozzle portion to discharge said intraocular lens; and a lens push-out mechanism to push out said intraocular lens placed on said lens placement portion, wherein said lens push-out mechanism comprises a plunger to push out said intraocular lens and a slider having a lens contact part larger than said plunger, while said slider is provided with an operating part projected outwardly from said main body, and wherein said intraocular lens is deformed by moving said slider by handling said operating part, and said intraocular lens is discharged from said nozzle portion by said plunger.

The invention according to a second aspect of the invention is characterized in that said operating part is projected outwardly from mutually opposed side surfaces of said main body.

The invention according to a third aspect of the invention is characterized in that said operating part is projected outwardly from one side of said main body.

The invention according to a fourth aspect of the invention is characterized in that said slider is provided with a lens holding part that holds one surface of an optic part of said intraocular lens and deforms said intraocular lens in a predetermined direction.

The invention according to a fifth aspect of the invention is characterized in that said lens holding part holds only the intraocular lens moved to said transition portion.

The invention according to a sixth aspect of the invention is characterized in that said lens holding part is connected with said slider via a hinge mechanism and is urged toward a sidewall of said main body, while said lens holding part is deformed toward the optic part of said intraocular lens through said transition portion.

The invention according to a seventh aspect of the invention is characterized in that said slider is provided with an inserting passage for inserting said plunger therethrough.

The invention according to an eighth aspect of the invention is characterized in that said intraocular lens comprises a pair of loop parts at said optic part, while said slider is provided with a loop guide to support said loop parts in such a condition that no physical load is applied thereto.

The invention according to a ninth aspect of the invention is characterized in that said slider is provided with a partition between said inserting passage and said loop guide.

The invention according to a tenth aspect of the invention is characterized in that a lock mechanism to lock said plunger is provided, said lock mechanism being constructed so that it can be unlocked by moving said slider.

The invention according to an eleventh aspect of the invention is characterized in that said lock mechanism is unlocked in association with the movement of said slider.

The invention according to a twelfth aspect of the invention is characterized in that said intraocular lens is sterilized with said intraocular lens being placed on said lens placement portion.

The invention according to a thirteenth aspect of the invention is characterized in that said main body is provided with a stopper to stop said slider at a predetermined position.

Effects of the Invention

According to the intraocular lens insertion device as set forth in the first aspect of the invention, the slider is moved by handling the operating part, and then the intraocular lens is discharged by the plunger. Accordingly, the push-out operation of the intraocular lens can be performed securely and safely, with a simpler structure. According to the intraocular lens insertion device as set forth in the second aspect of the invention, the slider can be moved by pinching the operating part with fingers from both sides, and thus reliability of the operation can be improved.

According to the intraocular lens insertion device as set forth in the third aspect of the invention, the slider can be moved by one hand, thus enabling more easier handling.

According to the intraocular lens insertion device as set forth in the fourth aspect of the invention, the intraocular lens can be folded in a predetermined direction, thus preventing operation troubles, ensuring even more reliable insertion of the intraocular lens.

According to the intraocular lens insertion device as set forth in the fifth aspect of the invention, the optic part of the intraocular lens is pressed down only at the time of use, and the lens holding part does not press down the optic part of the lens in an intact state, and thus permanent deformation of an elastic material can be suppressed even after a long period of preservation.

According to the intraocular lens insertion device as set forth in the sixth aspect of the invention, one surface of the intraocular lens moved to the transition portion can be pressed down with a simple structure. Further, since the lens holding part is urged toward the sidewall of the main body, there is a further advantage in terms of assembly process that the intraocular lens can be placed on a lens placement portion easily.

According to the intraocular lens insertion device as set forth in the seventh aspect of the invention, the slider is provided with the inserting passage, and thus the discharge of the intraocular lens can be ensured, by preventing the axial misalignment of the plunger.

According to the intraocular lens insertion device as set forth in the eighth aspect of the invention, the intraocular lens can be positioned in a predetermined position by the engagement of the loop parts with the loop guide. Further, since the loop parts are not pushed by the slider, deformation and damage of the loop parts can be prevented.

According to the intraocular lens insertion device as set forth in the ninth aspect of the invention, the plunger is not allowed to abut onto the loop parts, and thus, the loop parts can be prevented from being damaged by the pressing by the plunger.

According to the intraocular lens insertion device as set forth in the tenth aspect of the invention, it is possible to prevent an operator from pushing out the plunger accidentally prior to moving the slider, thus enabling the reliability of operation to be improved.

According to the intraocular lens insertion device as set forth in the eleventh aspect of the invention, the lock mechanism is unlocked in association with the movement of said slider, thus enabling the operability to be improved.

According to the intraocular lens insertion device as set forth in the twelfth aspect of the invention, it is possible to prevent the lens from being contaminated with other substances, thus improving safety.

According to the intraocular lens insertion device as set forth in the thirteenth aspect of the invention, the slider is stopped at a predetermined position by the stopper, thus enabling further improvement of the operational reliability.

BEST MODE FOR CARRYING OUT THE INVENTION

Next is a description of preferred embodiments of the present invention with reference to the attached drawings.

First Embodiment

Figure 1A:
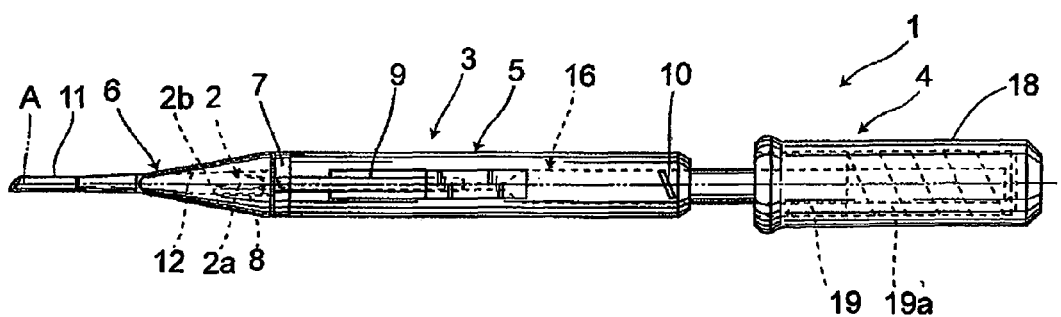
FIG. 1 is a diagram showing an overall structure of an intraocular lens insertion device according to a first embodiment of the present invention, in which (A) is a side view thereof, while (B) a plan view thereof.
Figure 1B:
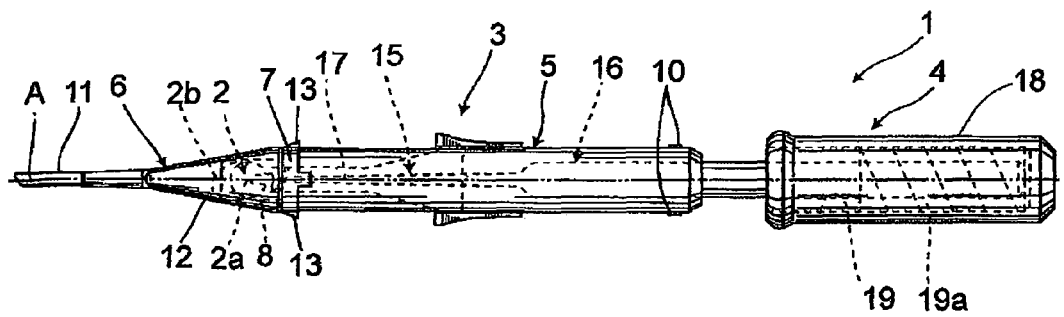

First, a first embodiment of the present invention is explained. An intraocular lens insertion device 1 shown in FIG. 1 is used to safely and quickly discharge into an eye a deformable intraocular lens 2 (hereinafter referred to as "lens 2"), and more particularly is a preset type intraocular lens insertion device 1 having the lens 2 preset in the intraocular lens insertion device 1. More specifically, the intraocular lens insertion device 1 is provided with a main body 3 that places the lens 2 therein and then inserts the lens 2 into an eye, and a lens push-out mechanism 4 that pushes out the lens 2 placed in the lens placement portion. In the meantime, for the lens 2 illustrated in the present embodiment is employed one comprising an optic part 2a and loop parts 2b.

Said main body 3 comprises a cylindrical proximal member 5 and a distal member 6 that is tapered relative to the proximal member 5. This proximal member 5 and the distal member 6 are detachably integrated with each other in an engagement section 7. It should be noted that the main body 3 may be made from various materials. For example, it may be made not only from stainless steel or titanium, but from a synthetic resin or the like.

The proximal member 5 comprises a lens placement portion 8 provided at one end thereof and a slit 9 formed in a cylindrical side wall and elongated in the longitudinal direction thereof. The lens placement portion 8 comprises a tabular member provided at the one end of the proximal member 5 in a protruding condition. The slit 9 is formed from an edge of the one end of the proximal member 5 to the substantial center thereof. Moreover, an engagement projection 10 with which a hereinafter-described grip section engages is provided on an outer peripheral surface of the proximal member 5'.

The distal member 6 comprises a nozzle portion 11 that is to insert the lens 2 placed in said lens placement portion 8 into an eye, and a transition portion 12 connecting said nozzle portion 11 with said proximal member 5. The transition portion 12 has a mortar shape such that it tapers toward a distal end, and is connected with the nozzle portion 11 at the distal end. The nozzle portion 11 is formed to have an outer diameter that is substantially of the same size as the width of an incision. The lens 2 is pushed out by the lens push-out mechanism 4 and then folded when it passes through said transition portion 12. The distal member 6 is provided with a stopper 13 for stopping a hereinafter-described slider in a predetermined position. This stopper 13 comprises a projection that is to engage with an operating part of the slider.

Said lens push-out mechanism 4 comprises the slider 15 to perform an initial operation for inserting the lens 2, and a plunger 16 to insert the lens 2 into an eye.

The plunger 16 is used to insert into an eye the lens 2 folded up by said slider 15, and comprises a push-out rod 17 to push out the lens 2, and a grip part 18 provided at the proximal end of said push-out rod 17. Said push-out rod 17 is loosely fitted into a hole 19 formed through the grip part 18, and is axially supported by the grip part 18 at the bottom of the hole 19. This hole 19 is formed with a female screw 19a. The female screw 19a formed in the grip part 18 is constituted so that it may screw together with said engagement projection 10. The engagement projection 10 is provided in the form of a partial male screw that is to be screwed into said female screw 19a. Due to the engagement projection 10 being provided in the form of a partial male screw thus way, it is possible to prevent the engagement projection 10 from interfering with said slit 9 etc., while ensuring the grip part to be pushed in reliably as a result of the engagement with the female screw 19a. Thus, such construction is provided that the grip part 18 pushes out the push-out rod 17 toward the direction of a lens movement axis A. The grip part 18 is formed in a shape that facilitates the pushing-out action of the plunger 16.

Figure 2:
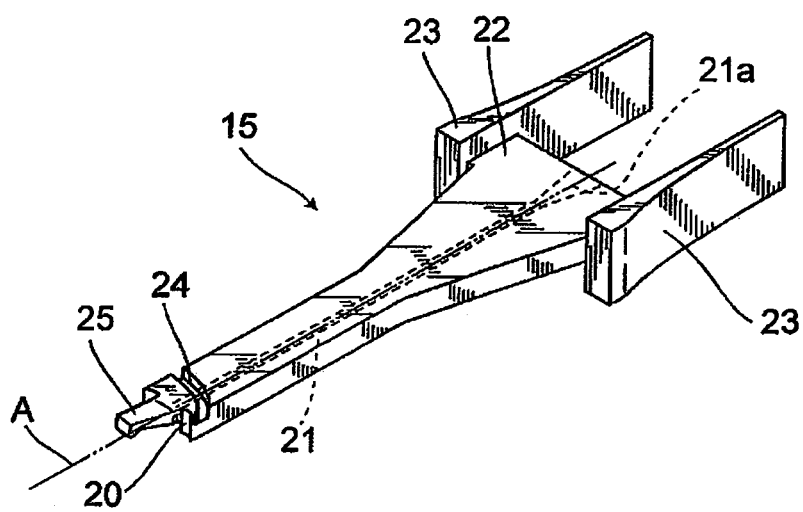
FIG. 2 is a perspective view showing a structure of a slider.

The slider 15 is constituted so that it can fold up the lens 2 in a predetermined direction, while pushing out the lens 2 placed in the lens placement portion 8 toward the distal end of the main body 3 without-applying local load to the lens 2, as shown in FIG. 2. This slider 15 includes a lens abutting portion 20 abutted on the lens 2 in a larger area than said plunger 16, a guide groove 21 serving as an inserting passage that supports said plunger 16 along the lens movement axis A, a wing part 22 that engages with the slit 9 provided in the main body 3 and guides the slider 15 along the lens movement axis A, an operating part 23 for pushing the slider 15 in and out, a loop guide 24 that fastens loop parts 2b of the lens 2, and a lens holding part 25.

Said lens abutting portion 20 is formed of a part of circle that has substantially the same radius of curvature as the outer diameter of the lens 2, such that it is allowed to come in surface contact with the lens 2, enabling the initial operation to be performed smoothly, without giving a local stress to the lens 2.

Said guide groove. 21 is formed so as to allow said plunger 16 to be slidable thereon, and to allow the distal end of said plunger 16 to be able to protrude from said lens abutting portion 20. The guide groove 21 is formed substantially in the center on one surface of the slider 15 over the entire length thereof, and comprises a groove arranged parallel to the lens movement axis A. The section of the guide groove 21 is substantially formed in the same shape as the contour of said plunger 16. A fan-shaped introduction passage 21a is formed at the proximal end of the guide groove 21. Thus, the push-out rod 17 is inserted through the guide groove 21 formed in said slider 15, and is allowed to slide within the guide groove 21 in the longitudinal direction of the slider 15. In the meantime, the guide groove 21 may be a through-hole that penetrates in parallel with the lens movement axis A.

The engagement of said wing part 22 with said slit 9 enables said slider 15 to be held substantially in the center of the main body 3, while enabling the slider 15 to move along the lens movement axis A. Accordingly, the plunger 16 is held in the center of the main body 3, and made movable along the lens movement axis A by the guide groove 21. The movement of the slider 15 is easily carried out through said operating part 23.

The operating part 23 is provided as a pair, at right and left sides relative to the lens movement axis A, and provided adjacent to the edge of said wing part 22 in a manner protruding outwardly from said proximal member 5. The operating part 23 is formed so as to bulge outwardly toward the distal end of said main body 3. Although not shown in the drawings, the surface of the operating part 23 is formed with two or more longitudinal grooves, extending substantially at right angles to the lens movement axis A.

Said loop guide 24 is formed on another surface of said slider 15 on which said guide groove 21 is not formed, and serves to fix the lens 2 by fastening the loop part 2b of the lens 2 therein. This loop guide 24 comprises a groove formed similar in shape to the curved loop part 2b, such that it is formed at the distal side of the slider 15 in such a curved shape that a physical load may not be applied to the loop part 2b.

Figure 3A:
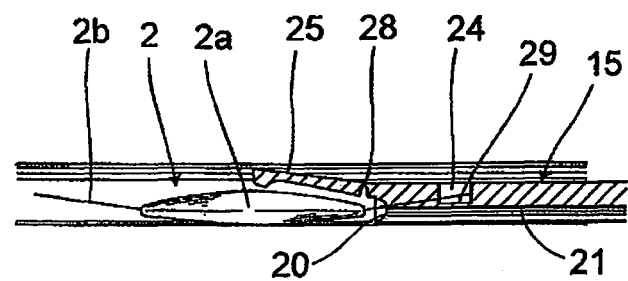
FIG. 3 is a partially enlarged view showing a positional relationship between the slider and a lens, in which (A) is a longitudinal cross-sectional view thereof, while (B) is a plan view thereof.
Figure 12A:
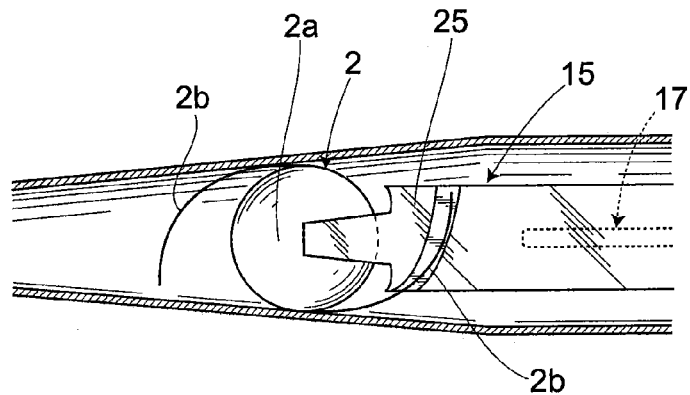
FIGS. 12A-12C are a sequence of sectional views with parts shown in full, in which the lens is deformed in part while being held by a part that is not deformed.
Figure 12B:
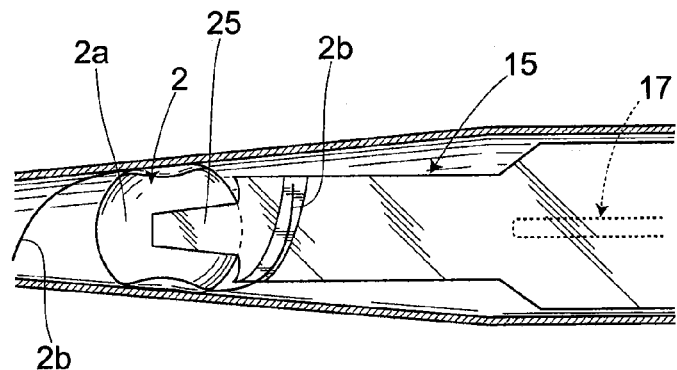
Figure 12C:
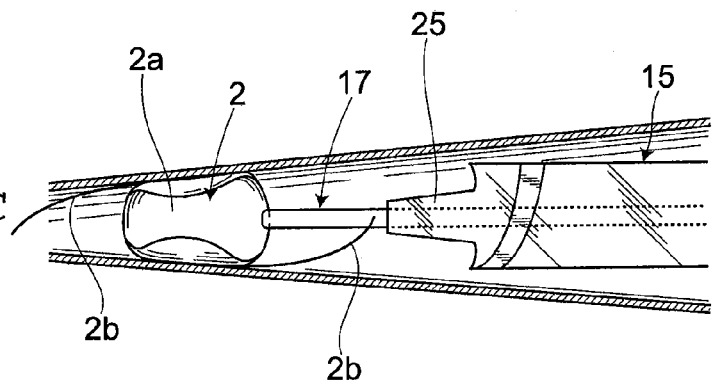

The lens holding part 25 enables the lens 2 to be folded up in a predetermined direction by pressingly holding one surface of the lens 2 only when pushing out the lens 2 as illustrated in FIGS. 12A-12C. That is, by pressing the one surface of the lens 2 that is to become a front surface thereof when inserted into an eye, using the lens holding part 25, the lens 2 is folded with the one surface thereof being inside, within the nozzle portion 11. Accordingly, the lens 2 can be deformed into such a shape that allows the lens 2 to be reliably inserted into a lens capsule. As shown in FIG. 12A, this lens holding part 25 is provided at the distal end of the slider 15 through a hinge mechanism 28 seen in FIG. 3A, and is provided in a manner capable of being tilted up and down in a side view. The hinge mechanism 28 is formed of a tapered groove provided by thinning a joint portion between the lens holding part 25 and the lens abutting portion 20 in the width direction of the slider 15. The lens holding part 25 is urged upwards in a side view, through this hinge mechanism 28, thus enabling the lens 2 to be folded in a predetermined direction by holding one side of the lens 2 when the lens 2 moves within the nozzle portion 11 as seen in FIGS. 12B-12C.

Moreover, said loop guide 24 is formed so that the plunger 16 may not abut to the loop part 2b. More specifically, a partition 29 is formed between the guide groove 21 formed on the one side of the slider 15 and the loop guide 24 formed on the other side of the slider 15. Accordingly, the plunger 16 is not allowed to abut to the loop part 2b engaged with the loop guide 24, thus preventing the damage of the loop part 2b caused by the loop part 2b being pushed by the plunger 16.

Figure 3B:
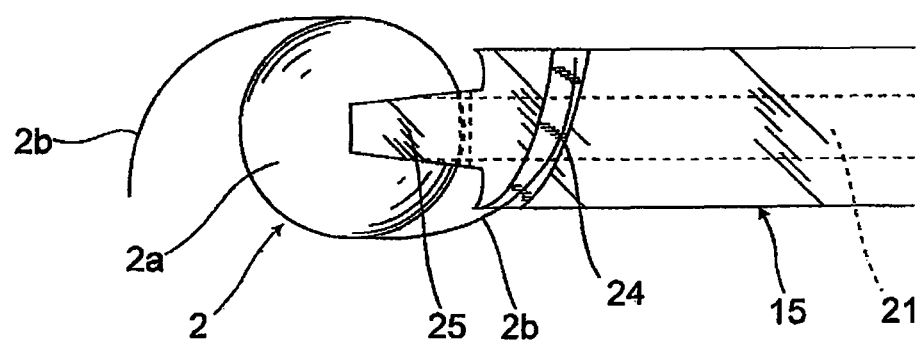

Next, is a description of an assembling procedure of the intraocular lens insertion device 1 structured in this way. First, the slider 15 is attached to the proximal member 5. In order to attach the slider 15 to the proximal member 5, the wing part 22 is allowed to be fitted into the slit 9 from the edge of the one end of the proximal member 5, and the slider 15 is pushed in up to the proximal end of the slit 9. Subsequently, the plunger 16 is inserted from the other end of the proximal member 5. At that moment, the distal end of the plunger 16 is aligned with such a position that it does not project from the distal end of the slider 15 placed in the proximal member 5. Then, the loop part 2b of the lens 2 is fastened by the loop guide 24 formed in the slider 15, and the lens 2 is placed in the lens placement portion 8. The lens 2 placed in the lens placement portion 8 is arranged in such a condition that the lens holding part 25 does not abut to the optic part 2a of the lens 2 due to the lens holding part 25 being urged toward an inner wall of the distal member 6 by the hinge mechanism 28, as shown in FIG. 3 (A). Subsequently, the distal member 6 and the proximal member 5 are integrated with each other in the engagement section 7. Thus, the intraocular lens insertion device 1 can be assembled reliably, without applying a load to the lens 2.

Then, the intraocular lens insertion device 1 with the lens 2 being attached as mentioned above, is sterilized, which is carried out by placing the intraocular lens insertion device 1 into a sterilization bag (not shown), and filling the interior of the bag with ethylene oxide gas (hereinafter called EOG). Since EOG enters into the intraocular lens insertion device 1 from the slit 9 due to the provision of the slit 9 in the sterilization bag filled with EOG, it is possible to introduce EOG into the inside even though no specific hole for introducing sterilization EOG into the inside is provided, thus ensuring full sterilization up to the inside.

Figure 4A:
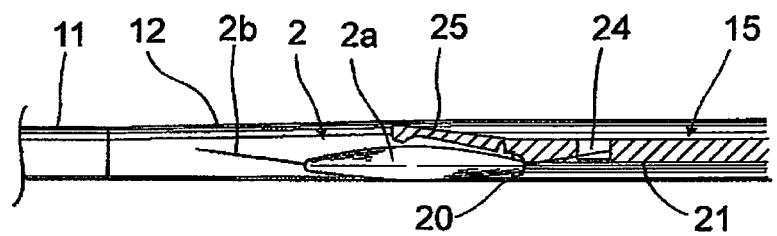
FIG. 4 is a partially enlarged longitudinal section illustrating the operation of the push out mechanism progressively.
Figure 4B:
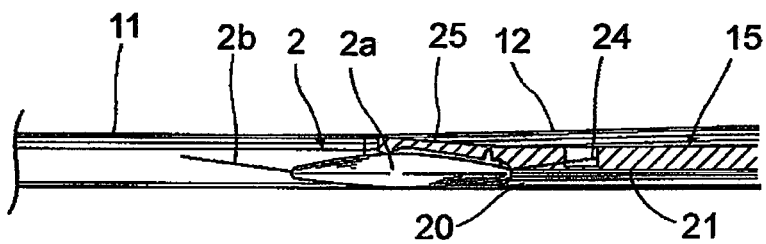
Figure 4C:
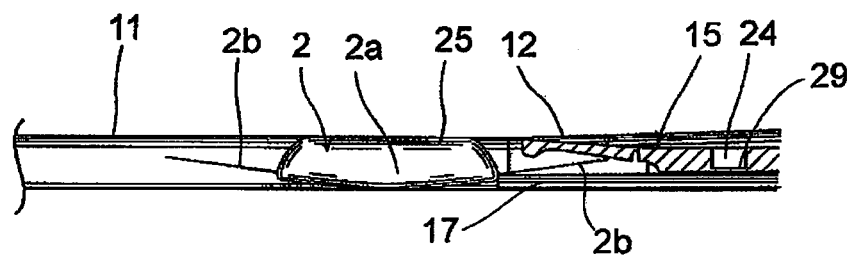
Figure 5A:
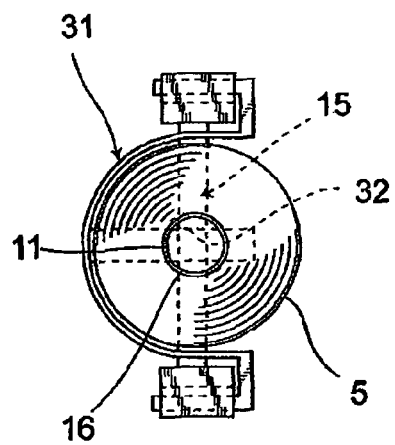
FIG. 5 is a diagram showing an intraocular lens insertion device according to a second embodiment of the present invention, in which (A) is a front view thereof, while (B) a bottom view thereof.
Figure 5B:
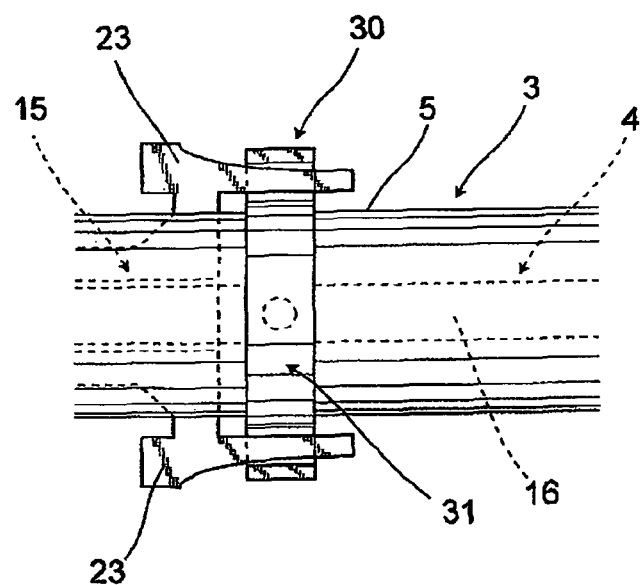

Next, the action of the above-mentioned structure will be explained. After taking out the intraocular lens insertion device 1 from the sterilization bag, the operating part 23, at first, is pushed out and thus the slider 15 is moved in the direction of the lens movement axis A. Upon the movement of the slider 15, the lens holding part 25 is pressed by the inner wall of the transition portion 12, and tilted downward in a side view, thereby pressingly holding the one surface of the optic part 2a of the lens 2 (FIG. 4 (B)). When the slider 15 pushes out the lens 2, the lens holding part 25 presses down the one surface of the optic part 2a, thus enabling the lens 2 to be folded in the predetermined direction as illustrated in FIGS. 12A-12C. The plunger 16 is pushed out after the slider 15 abuts to the stopper 13 and then stops (FIG. 4 (C)). In order to push out the plunger 16, first, the grip part 18 is pushed out, and the female screw 19a is engages with the engagement projection 10 by screwing. Subsequently, the grip part 18 is rotated. Upon the rotation of the grip part 18, the grip part 18 is moved in the direction of the lens movement axis A from the other end of the proximal member 5, and thus the push-out rod 17 is pushed by the grip part 18 to move in the direction of the lens movement axis A, thus pushing out the plunger 16. In this way, the lens 2 is folded up by being pushed by the plunger 16 and passing through the thin nozzle portion 11 as seen in FIG. 12B. Thus, pushing out the plunger 16 further with the lens 2 being folded allows the lens 2 to be inserted into an eye. Since the partition 29 is provided between the guide groove 21 and the loop guide 24 when pushing out the plunger 16, it is possible to prevent the damage of the loop part 2b due to the plunger 16 not pushing the loop part 2b as seen in FIG. 12C.

According to the present embodiment as mentioned above, the intraocular lens insertion device 1 comprises: the main body 3, including the lens placement portion 8 that places the lens 2 therein, the transition portion 12 to deform said lens 2, and the nozzle portion 11 to introduce said lens 2; and the lens push-out mechanism 4 that pushes out the lens 2 placed in said lens placement portion 8, wherein said lens push-out mechanism 4 comprises: the plunger 16 that pushes out the lens 2; and the slider 15 having the lens abutting portion 20 larger than this plunger 16, while said slider 15 includes the operating part 23 projected outwardly from said main body 3, and the lens 2 is deformed by moving said slider 15 through the operation of said operating part 23 so that said lens 2 is discharged from said nozzle portion 11 by said plunger 16, whereby the discharge operation of the lens 2 can be performed reliably and safely with simpler structure.

Moreover, since said operating part 23 is provided so as to project outwardly from each opposite side surface of said main body 3, it is possible to move the slider 15 with the operating parts 23 being pinched with fingers from both sides, thereby enabling the improvement of the reliability of the operation.

Still moreover, since said slider 15 comprises the lens holding part 25 that presses down the one surface of the optic part 2a of the lens 2 to deform said lens 2 in the predetermined direction, it is possible to fold up the lens 2 in the predetermined direction, thus preventing problems associated therewith, enabling the lens 2 to be inserted into an eye more reliably.

Further, since said lens holding part 25 is constituted so as to press down only the lens 2 that has moved to the transition portion 12, the optic part 2a of the lens 2 is pressed down only at the time of use, and the lens holding part 25 does not press down the optic part 2a of the lens 2 in an intact state, and thus permanent deformation of an elastic material can be suppressed even after a long period of preservation.

Still further, said lens holding part 25 is connected with said slider 15 through the hinge mechanism 28, and is urged toward the side wall of said main body 3 so that it may be deformed toward the optic part 2a of said lens 2 through said transition portion 12, it is possible to press down the one surface of the lens 2 reliably, only when it moves to the transition portion 12, with simpler structure.

Furthermore, since said slider 15 comprises the guide groove 21 for inserting said plunger 16 therethrough, it is possible to prevent axial misalignment of the plunger 16, ensuring the reliable discharge of the lens 2.

Also, said lens 2 comprises the optic part 2a with a pair of the loop parts 2b, while said slider 15 comprises the loop guide 24 that supports said loop parts 2b in such a condition that no physical load is applied thereto, whereby it is possible to position the lens 2 in a predetermined location by engaging the loop parts 2b with the loop guide 24, while enabling the preventing of the deformation of the loop parts 2b due to the loop parts 2b being not pressed by the slider 15.

Besides, since said slider 15 is formed with the partition 29 between said inserting passage and said loop guide 24, the slider 15 does not abut to the loop part 2b, thus enabling the loop part 2b to be prevented from being damaged by the pressing by the slider 15.

Moreover, since the lens 2 is sterilized with the same being placed in the lens placement portion 8, it is possible to prevent the same from being contaminated with other substances, thus improving safety.

Also, since said main body 3 comprises the stopper 13 that stops said slider 15 in a predetermined position, stopping the slider 15 in a predetermined position using the stopper 13 enables the further enhancement of the reliability of the operation.

Still also, since the lens holding part 25 is provided in a manner capable of being tilted up and down through the hinge mechanism 28, the optic part 2a of the lens 2 is pressed down only when pushing out the slider 15 to move the lens 2, thus enabling the lens 2 to be preserved without applying unnecessary load thereto.

Alternatively, the operating part 23 may be projected outwardly from only one side of said proximal member 5. In that case, the operating part 23 can be operated with one hand to move the slider 15, usability of the device can be improved.

As the operating part 23 is formed so as to bulge outwardly toward the distal end of said main body 3, while the surface thereof is formed with two or more longitudinal grooves, increased frictional resistance is resulted when operating the operating part 23 with fingers, thus preventing slippage, enabling the improvement of the reliability of operation.

Besides, since the fan-shaped introduction passage 21a is provided at the proximal end of the guide groove 21, the plunger 16 can be easily inserted through the guide groove 21 when attaching the plunger 16.

In addition, since the plunger 16 is axially supported by the grip part 18, the plunger 16 does not rotate even when the push-out rod 17 is pushed out in the direction of the lens movement axis A while rotating the grip part 18, whereby the lens 2 can be pushed out smoothly, without the plunger 16 rotating.

Second Embodiment

Next, a second embodiment of the present invention will be explained. The same portions as those described in the above-mentioned structure will be designated by the same reference numerals, and the duplicate description thereof will be omitted. Specifically, the intraocular lens insertion devices of the first and second embodiments are common in the sense that they comprise the main body 3 for placing the lens 2 and inserting the lens 2 into an eye; and the lens push-out mechanism 4 that pushes out the lens 2 placed in said lens placement portion 8, while the second embodiment differs from the first embodiment only in that it comprises a lock mechanism 30.

The lock mechanism 30 locks the plunger 16, and is capable of being unlocked only when the slider 15 is pushed out. The lock mechanism 30 comprises a lock member 31 provided in a detachable manner and a lock reception portion 32 provided in the plunger 16.

Figure 6:
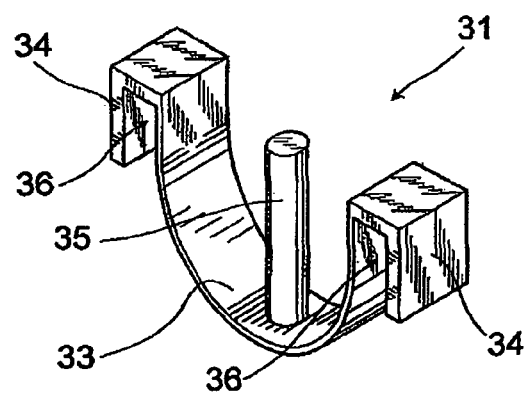
FIG. 6 is a perspective view showing a structure of a locking member.

As shown in FIG. 6, the lock member 31 comprises a locking body 33 that is formed in a curved shape, an arm 34 integrally provided at both sides of the locking body 33, and a locking element 35 vertically provided substantially in the center of an inside area of the locking body 33. The locking body 33 has a curved shape slightly larger than the contour of the cylindrical main body 3, and is fitted thereto from outside. The arms 34 are formed by folding the ends of the locking body 33 so that a clearance 36 to insert said operating part 23 of the slider 15 therethrough is formed between each arm 34 and the outside portion of the locking body 33. The locking element 35 is composed of a cylindrical member extending vertically from the inside of the locking body 33, and is fitted to the lock reception portion 32 provided in the plunger 16. The lock reception portion 32 comprises a through-hole formed in the plunger 16. Alternatively, the locking member 35 is not limited to take a columnar shape, but may be also formed in a shape of a polygon, such as a square pillar. In that case, the lock reception portion 32, needless to say, is formed in accordance with the shape of the locking element 35.

Figure 7A:
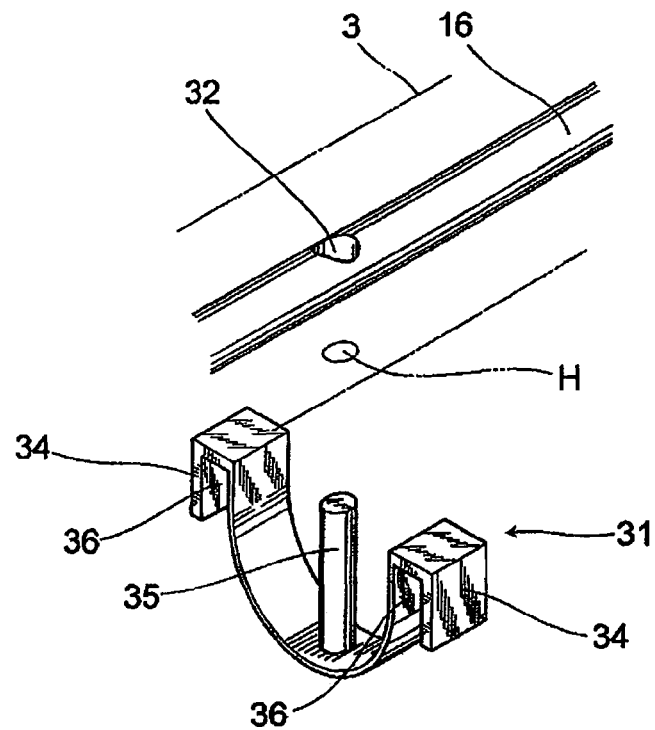
FIG. 7 is a perspective view progressively illustrating the locking operation of a plunger.
Figure 7B:
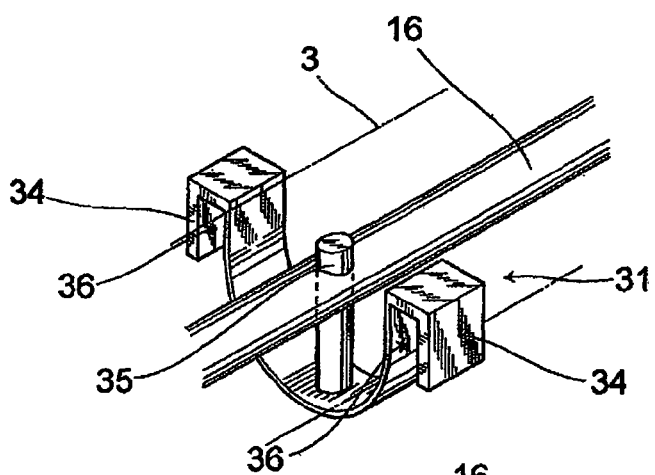
Figure 7C:
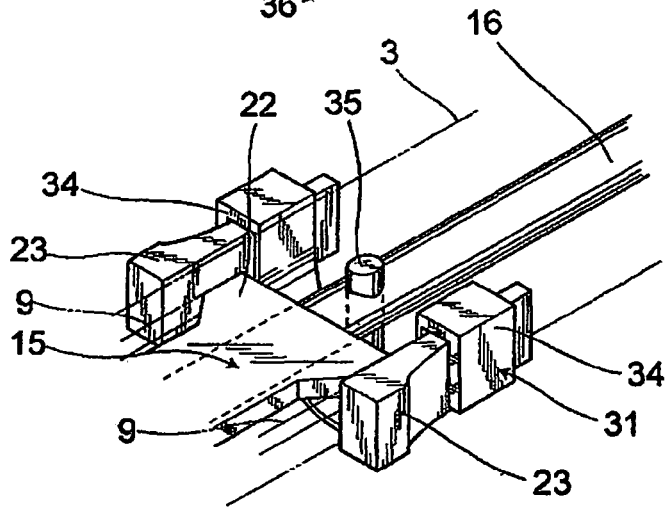
Figure 8A:
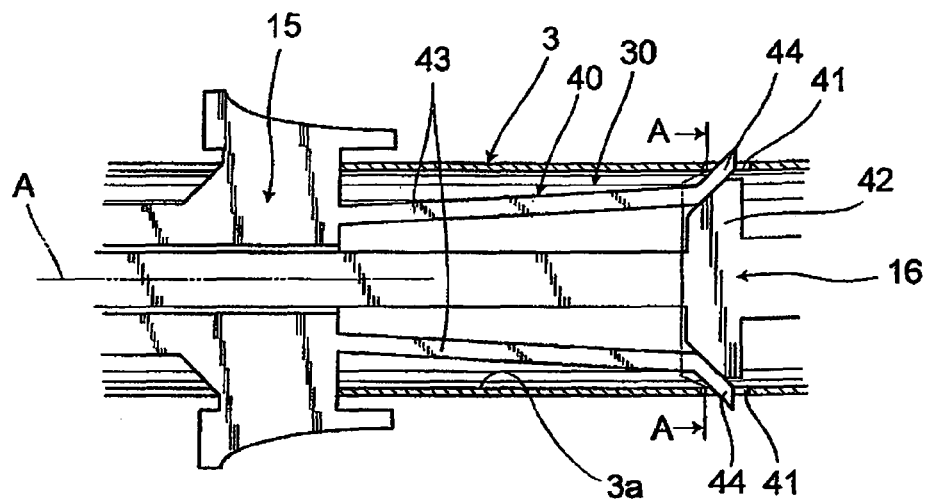
FIG. 8 is a diagram showing an intraocular lens insertion device according to a third embodiment of the present invention, in which (A) is a fragmentary transverse section thereof, while (B) is a longitudinal section of a plunger, and (C) is a cross-section taken along A-A line in (A), respectively.
Figure 8B:
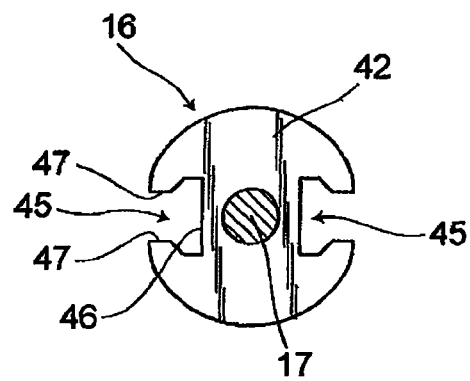
Figure 8C:
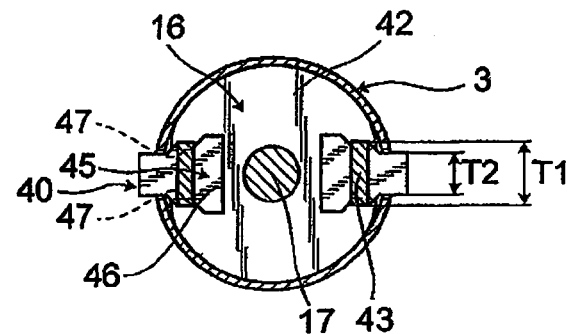

Next is a description of a procedure for attaching the above-structured lock mechanism 30 with reference to FIG. 7. First, the lock member 31 is attached, from the bottom side, to the main body 3 with the plunger 16 inserted thereinto (FIG. 7 (A)). That is, the locking element 35 is inserted from a hole H formed beforehand on the main body 3, and then the distal end of the locking element 35 is fitted to the lock reception portion 32 provided in the plunger 16, to thereby attach the lock member 31 to the main body 3 (FIG. 7 (B)). Thus way, the plunger 16 is locked relative to the main body 3 through the locking element 35 inserted through the hole H formed in the main body 3.

Subsequently, the wing part 22 is allowed to engage with said slit 9, and then the slider 15 is pushed in up to the proximal end of the slit 9. When the slider 15 is pushed in, the operating part 23 is inserted into the clearance 36 formed between the arm 34 and the outside of the locking body 33 (FIG. 7 (C)). When the operating part 23 is inserted into the clearance 36 thus way, the lock member 31 is fixed by the slider 15. In other words, the lock member 31 is fixed by the arm 34 engaging with the operating part 23 of the slider 15 under such a condition that the locking body 33 is abutted to the main body 3.

The lock mechanism 30 thus attached is unlocked in accordance with the reverse procedure to the above-mentioned procedure. First, the slider 15 is pushed out toward the distal end. Then, the operating part 23 is moved away from the arm 34, and thus the engagement therebetween is released. The lock member 31 can be pulled apart toward the bottom side, only after the engagement of the operating part 23 with the arm 34 is released. Thus, since the lock mechanism 30 can be unlocked only when the slider 15 is pushed out toward the distal side, i.e., only when the lens 2 is inserted into an eye, and thus improved safety can be achieved.

As discussed above, according to the present embodiment, the intraocular lens insertion device 1 comprises the lock mechanism 30 to lock said plunger 16, and said lock mechanism 30 is constituted such that it is able to be unlocked by moving the slider 15, whereby it is possible to prevent an operator from pushing out the plunger 16 accidentally prior to moving the slider 15, thus enabling the safety and reliability of operation to be improved.

Third Embodiment

Next, a third embodiment of the present invention will be explained. The same portions as those described in the above-mentioned structure will be designated by the same reference numerals, and the duplicate description thereof will be omitted. Specifically, the intraocular lens insertion device of the third embodiment is the same as the ones of the foregoing embodiments in that it comprises the main body 3 for placing the lens 2 and inserting the lens 2 into an eye; and the lens push-out mechanism 4 that pushes out the lens 2 placed in said lens placement portion 8, except the structure of the lock mechanism 30 described in the second embodiment.

The lock mechanism 30 serves to locks the plunger 16, and is capable of being unlocked in association with the operation for pushing out the slider 15. This lock mechanism 30 comprises an engagement portion 40 provided in the slider 15, an engagement hole 41 for engagement with the engagement portion 40, and a disk part 42 provided in the plunger 16.

The engagement portion 40 is provided as one pair, on right and left sides with respect to the lens movement axis A, respectively, and comprises a rocking piece 43 elongated from the rear end of the slider 15 toward the other end side of the main body 3, and a latching piece 44 provided at the distal end of the rocking piece 43. This latching piece 44 is bent toward the outside of the main body 3, and locked through the engagement with said engagement hole 41, protruding therefrom toward the outside of the main body 3. The rocking piece 43 is provided in a manner capable of rocking toward the inside and outside of the main body 3 in a plan view, and thus it is formed so that it may be arranged parallel to the lens movement axis A when said latching piece 44 abuts to the inner side 3a of the main body 3. The width T1 of the rocking piece 43 is formed greater than the width T2 of the latching piece 44. In the meantime, the latching piece 44 is constituted so that the angle of the rocking piece 43 relative to the latching piece 44 is an obtuse angle.

The disk part 42 is formed concentrically relative to the push-out rod 17, and is provided with a pair of transverse grooves on right and left sides around the push-out rod 17. Each transverse groove 45 is similar in shape to said engagement portion 40, and is provided with a bottom 46 that is broadened toward the center of the push-out rod 17 and a pair of protrusions 47 in a peripheral edge of the disk part 42. Thus, the plunger 16 is locked by the protrusions 47 abutting to said rocking piece 43.

Figure 9A:
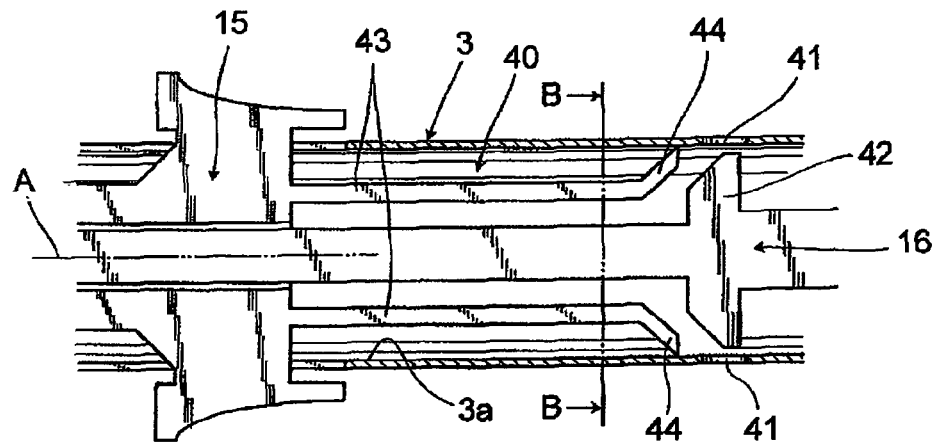
FIG. 9 is a diagram showing the intraocular lens insertion device in an unlocked state, in which (A) is a transverse cross-section thereof, while (B) is a cross-section taken along B-B line in (A).
Figure 9B:
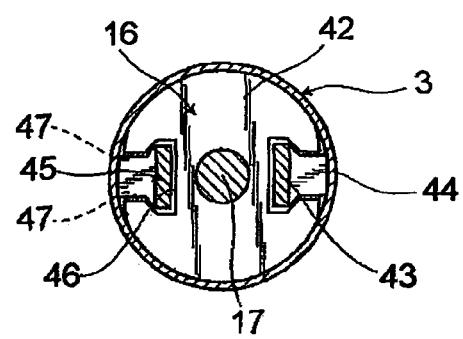
Figure 10:
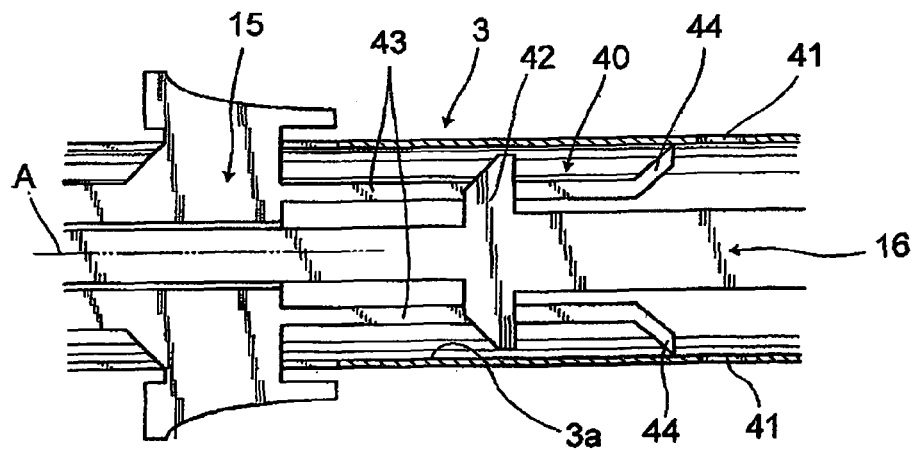
FIG. 10 is a transverse cross-section showing the intraocular lens insertion device with the plunger being pushed out in an unlocked state.

Next is a description of the action of the above-mentioned structure. First, the slider 15 is pushed out toward the distal end. When the slider 15 is pushed out thus way, the latching piece 44 then abuts onto the engagement hole 41 so that it is arranged at an obtuse angle to the rocking piece 43, thereby allowing the same to slide along the inner edge of the engagement hole 41. Then, the rocking piece 43 is rocked toward the inside of the main body 3. When the slider 15 is further pushed out toward the distal end, the latching piece 44 is allowed to go beyond the engagement hole 41, so that the distal end of the latching piece 44 abuts on the inside surface of the main body 3. When the distal end of the latching piece 44 abuts on the inside surface of the main body 3 thus way, the rocking piece 43 is arranged parallel to the lens movement axis A, and thus the rocking piece 43 moves to the position of the bottom 46 of each transverse groove 45 as viewed from front, thus releasing the lock (FIG. 9). Upon the releasing of the lock in this way, the plunger 16 is allowed to push out the lens 2 due to the disk part 42 passing the engagement portion 40 (FIG. 10).

According to the present embodiment, the intraocular lens insertion device 1 is constituted such that said lock mechanism 30 is unlocked in association with the movement of said slider 15, thus enabling the operability to be improved.

Alternatively, a guide groove (not shown) to guide the latching piece 44 may be provided inside the main body 3. Such guide groove, extending from the engagement hole 41 in the direction of the lens movement axis A, comprises a groove with which the distal end of said latching piece 44 engages. The provision of such guide groove on the inside of the main body 3 can prevent the slider 15 from rotating about the lens movement axis A even when the lock is released by the movement of the slider 15, thereby ensuring the disk part 42 to pass the engagement portion 40 in order for the plunger 16 to be able to push out the lens 2.

The present invention is not limited to the foregoing embodiments, and various modifications are possible within the scope of the present invention. Although the proximal member 5 and the plunger 16 are screwed together in the foregoing embodiments, the invention should not be limited thereto, but the plunger 16 may be provided with a packing so that it may slide within the proximal member 5 through such packing. Moreover, although the locking element 35 is a columnar member and the lock reception portion 32 is a through-hole formed in the plunger 16 in the foregoing embodiment, the invention should not be limited thereto, but the locking element 35 may be a two-forked support pillar member, while the lock reception portion 32 may be a groove formed at a right angle to the longitudinal direction of the plunger 16. Alternatively, an urging member such as a coil spring may be mounted in order to urge the plunger 16 toward the proximal end of the main body 3.

Fourth Embodiment

Figure 11A:
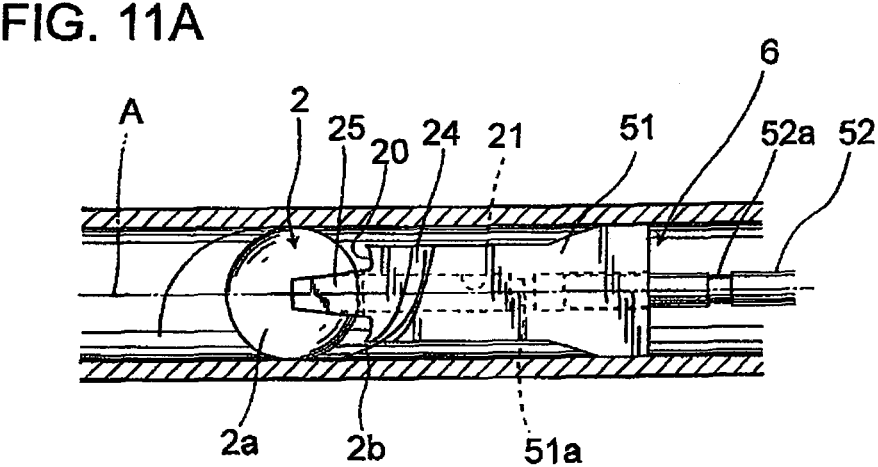
FIG. 11 is a transverse cross-section showing an intraocular lens insertion device according to a fourth embodiment of the present invention, in which (A) is a view showing a state prior to the interlocking of the slider with the plunger, while (B) is a view showing the slider and the plunger moving together after interlocked with each other.

Next, a fourth embodiment of the present invention will be explained with reference to FIG. 11(A). The same portions as those described in the above-mentioned structure will be designated by the same reference numerals, and the duplicate description thereof will be omitted. The slider 51 according to the present embodiment is not provided with the operating part, and a lens push-out mechanism 6 is provided with a slider 51 and a plunger 52 in a manner capable of interlocking with each other. Said slider 51 is provided with the guide groove 21 formed along the lens movement axis A, while a convex portion 51a is provided in the guide groove 21. A concave portion 52a that engages with said convex portion 51a is formed in a circumference of said plunger 52. This plunger 52 is inserted through said guide groove 21, and is arranged in a manner capable of moving back and forth with respect to the lens movement axis A.

Figure 11B:
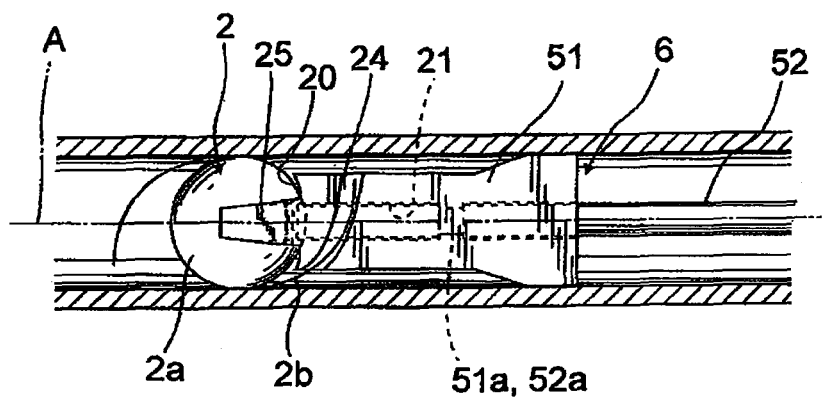

When the plunger 52 is moved forth in the above-structured lens push-out mechanism 6, the concave portion 52a is allowed to engage with the convex portion 51a. Upon the engagement of the concave portion 52a with the convex portion 51a, the slider 51 is interlocked with the plunger 52 and then moves in the direction of the lens movement axis A (FIG. 11 (B)). The slider 51 moved in the direction of the lens movement axis A together with the plunger 52 is allowed to stop when it abuts onto a stopper. When the plunger 52 is further pushed in toward the direction of the lens movement axis A, the concave portion 52a is disengaged from the convex portion 51a, and thus the engagement of the slider 51 with the plunger 52 is released. As a result, the plunger 52 becomes movable independently, and the lens 2 is pushed out by the plunger 52.

Even for the slider 51 that is not provided with the operating part, the loop guide 24 and the lens holding part 25 may be provided.

We claim:

1. An intraocular lens insertion device for use with an intraocular lens having an optic part with a first surface, a second surface opposite the first surface, and an outer edge between the first and second surfaces, said insertion device comprising:
    a main body defining a lens travelling axis and including a lens placement portion configured to have the intraocular lens placed thereon, a transition portion to deform said intraocular lens', a nozzle portion to discharge said intraocular lens and a distal end; and
    a lens push-out mechanism to push out said intraocular lens placed on said lens placement portion,
    wherein said lens push-out mechanism includes a plunger to push out said intraocular lens and a slider having a lens contact part larger than said plunger, wherein said slider is provided with an operating part projected outwardly from said main body and a lens holding part that holds one surface of an optic part of said intraocular lens,
    wherein said main body transition portion and said slider lens holding part are respectively sized, shaped and arranged relative to one another such that as said slider pushes said intraocular lens along the lens travelling axis through said transition portion and towards said nozzle, said slider lens holding part will apply force to said first surface of said intraocular lens optic part in a direction transverse to said lens travelling axis while said transition portion engages laterally spaced portions of said outer edge thereby gradually folding said intraocular lens about said lens holding part as said intraocular lens moves toward the distal end of said main body through said transition portion, and
    wherein said intraocular lens is discharged from said nozzle portion by said plunger after said lens is folded by said transition portion and said slider.

2. The intraocular lens insertion device according to claim 1, wherein said lens holding part holds only the intraocular lens moved to said transition portion.

3. The intraocular lens insertion device according to claim 2, wherein said lens holding part is connected with said slider via a hinge mechanism and is urged toward a sidewall of said main body, while said lens holding part is deformed toward the optic part of said intraocular lens through said transition portion.

4. The intraocular lens insertion device according to claim 1, wherein said lens holding part only holds said first surface of the said intraocular lens optical part.

5. The intraocular lens insertion device according to claim 1, wherein the slider is configured such the lens holding part will extend over the first surface when the lens contact part engages the edge of the outer edge of the intraocular lens.

6. The intraocular lens insertion device according to claim 1, wherein the part of the transition portion that engages laterally spaced portions of said outer edge is not movable relative to the nozzle portion.

7. The intraocular lens insertion device according to claim 1, further comprising:
    an intraocular lens, having an optic part with a first surface, a second surface opposite the first surface, and an outer edge between the first and second surfaces, stored in the lens placement portion.

8. An intraocular lens insertion device for use with an intraocular lens having an optic part with a first surface, a second surface opposite the first surface, and an outer edge between the first and second surfaces, said insertion device comprising:
    a main body defining a lens travelling axis and including a lens placement portion configured to have the intraocular lens placed thereon, a transition portion to deform said intraocular lens, a nozzle portion to discharge said intraocular lens and a distal end;
    a plunger to push out said intraocular lens; and
    a slider having a lens contact part larger than said plunger and a lens holding part that holds said first surface of said optic part of said intraocular lens, and
    wherein said main body transition portion and said slider lens holding part are respectively sized, shaped and arranged relative to one another such that as said slider pushes said intraocular lens along the lens travelling axis through said transition portion and towards said nozzle, said slider lens holding part will apply force to said first surface of said intraocular lens optic part in a direction transverse to said lens travelling axis while said transition portion engages laterally spaced portions of said outer edge thereby gradually folding said intraocular lens about said lens holding part as said intraocular lens moves toward the distal end of said main body through said transition portion, and
    wherein said intraocular lens is discharged from said nozzle portion by said plunger after said lens is folded by said transition portion and said slider.

9. The intraocular lens insertion device according to claim 8, wherein said lens holding part holds only the intraocular lens moved to said transition portion.

10. The intraocular lens insertion device according to claim 9, wherein said lens holding part is connected with said slider via a hinge mechanism and is urged toward a sidewall of said main body, while said lens holding part is deformed toward the optic part of said intraocular lens through said transition portion.

11. The intraocular lens insertion device according to claim 8, wherein said lens holding part only holds said first surface of the said intraocular lens optical part.

12. The intraocular lens insertion device according to claim 8, wherein the slider is configured such the lens holding part will extend over the first surface when the lens contact part engages the edge of the outer edge of the intraocular lens.

13. The intraocular lens insertion device according to claim 8, wherein the part of the transition portion that engages laterally spaced portions of said outer edge is not movable relative to the nozzle portion.

14. The intraocular lens insertion device according to claim 8, further comprising:
   an intraocular lens, having an optic part with a first surface, a second surface opposite the first surface, and an outer edge between the first and second surfaces, stored in the lens placement portion.

* * * * *